(12) United States Patent
Lukomski et al.

(10) Patent No.: US 11,560,419 B2
(45) Date of Patent: Jan. 24, 2023

(54) TARGETING TUMOR MICROENVIRONMENTS WITH RECOMBINANT PROKARYOTIC COLLAGEN-LIKE PROTEINS

(71) Applicant: WEST VIRGINIA UNIVERSITY, Morgantown, WV (US)

(72) Inventors: Slawomir Lukomski, Morgantown, WV (US); Dudley H. McNitt, Morgantown, WV (US)

(73) Assignee: WEST VIRGINIA UNIVERSITY, Morgantown, WV (US)

( * ) Notice: Subject to any disclaimer, the term of this patent is extended or adjusted under 35 U.S.C. 154(b) by 0 days.

(21) Appl. No.: 16/725,142

(22) Filed: Dec. 23, 2019

(65) Prior Publication Data

US 2020/0199200 A1    Jun. 25, 2020

Related U.S. Application Data

(60) Provisional application No. 62/783,843, filed on Dec. 21, 2018.

(51) Int. Cl.
| | |
|---|---|
| C07K 14/315 | (2006.01) |
| C07K 14/78 | (2006.01) |
| C12N 15/74 | (2006.01) |
| A61K 38/00 | (2006.01) |

(52) U.S. Cl.
CPC ............ *C07K 14/78* (2013.01); *C12N 15/746* (2013.01); *A61K 38/00* (2013.01); *C07K 2317/24* (2013.01)

(58) Field of Classification Search
None
See application file for complete search history.

(56) References Cited

U.S. PATENT DOCUMENTS

| | | | | |
|---|---|---|---|---|
| 5,882,645 | A * | 3/1999 | Toth ................... | A61K 47/6911 424/194.1 |
| 6,953,839 | B2 * | 10/2005 | Hook ..................... | C07H 21/04 530/350 |
| 7,238,783 | B2 * | 7/2007 | Hook ..................... | C07H 21/04 530/350 |
| 7,544,780 | B2 * | 6/2009 | Hook ..................... | C07K 14/78 530/350 |
| 7,700,731 | B2 * | 4/2010 | Hook ..................... | C07K 14/78 530/356 |

OTHER PUBLICATIONS

An, Bo et al.; "Engineered recombinant bacterial collagen as an alternative collagen based biomaterial for tissue engineering." Front. Chem. (2014) 2(40) 1-5.*
McNitt, Dudley H. et al; "Adaptation of the group a *Streptococcus* adhesion scl1 to bind fibronectin type iii repeates within wound associated extracellular matrix, implications for cancer therapy." Mol. Microbiol. (2019) 112(3) p. 800-819.*
Caswell, Claton C. et al; "Scl1, the multifunctional adhesion of group a *Streptococcus* selectively binds cellular fibrnectin and laminin , and mediates pathgen internalization by human cells." FEMS Microbiol. Lett. (2010) 3030(1) p. 61-68.*
Yampolsky, Lev Y. and Stolzfus, Arlin; "The exchangeability of amino acids in proteins." Genetics (2005) 170 p. 1459-1472.*
Haikarainen, Teemu et al, "Magnetic properties and structural characterization of iron oxide nanoparticles fromed by *Streptococcus suisdpr* and four mutants." J. Biol. Inorg. Chem. (2011) 16 p. 799-807.*
Seo, Neungseon et al; "An engineered alpha1 integrin binding collagenous sequence." J. Biol. Chem. (2010) 285(40) p. 31046-31054.*
Birchler, et al., "Expression of the extra domain B of fibronectin, a marker of angiogenesis, in head and neck tumors", Laryngoscope, 113(7), pp. 1231-1237. (2003).
Bo An, et al., "The influence of specific binding of collagen-silk chimeras to silk biomaterials on hMSC behavior", Biomaterials, 34(2), pp. 402-412. (Jan. 2013).
Bronk, et al., "A multifunctional streptococcal collagen-mimetic protein coating prevents bacterial adhesion and promotes osteoid formation on titanium", Acta Biomaterialia, 10(7), pp. 3354-3362. (2014).
Browning, et al., "Multilayer vascular grafts based on collagen-mimetic proteins", Acta Biomaterialia, 8(3), pp. 1010-1021. (2014).
Caswell, et al., "Identification of the first prokaryotic collagen sequence motif that mediates binding to human collagen receptors, integrins α2β1 and α11β1", The Journal of Biological Chemistry, 283(52), pp. 36168-36175. (2008).
Caswell, et al., "Scl1, the multifunctional adhesin of group A *Streptococcus*, selectively binds cellular fibronectin and laminin, and mediates pathogen internalization by human cells", FEMS Microbiology Letters, 303(1), pp. 61-68. (2010).
Caswell, et al., "Sell-dependent internalization of group A *Streptococcus* via direct interactions with the α2β1 integrin enhances pathogen survival and re-emergence", Molecular Microbiology, 64(5), pp. 1319-1331. (2007).
Cosgriff-Hernandez, et al., "Bioactive hydrogels based on Designer Collagens", Acta Biomaterialia, 6(10), pp. 3969-3977. (2010).
Grana, et al., "Pretargeted adjuvant radioimmunotherapy with yttrium-90-biotin in malignant glioma patients: a pilot study", British Journal of Cancer, 86(2), pp. 207-212. (2002).
Gutbrodt, et al., "Antibody-Based Delivery of Interleukin-2 to Neovasculature Has Potent Activity Against Acute Myeloid Leukemia", Science Translational Medicine, 5(201), 11 pages. (2013).
Hemmerle, et al., "The antibody-based targeted delivery of TNF in combination with doxorubicin eradicates sarcomas in mice and confers protective immunity", British Journal of Cancer, 109(5), pp. 1206-1213. (2013).

(Continued)

*Primary Examiner* — Fred H Reynolds
(74) *Attorney, Agent, or Firm* — Kramer & Amado, P.C.

(57) ABSTRACT

A recombinant collagen-like protein comprising a binding domain having binding capacity for both extra domain A and extra domain B-containing variants of cellular fibronectin. Cancer may be treated BY administering the recombinant collagen-like protein to a patient.

18 Claims, 3 Drawing Sheets

Specification includes a Sequence Listing.

(56) References Cited

OTHER PUBLICATIONS

Ko, et al., "A multimodal nanoparticle-based cancer imaging probe simultaneously targeting nucleolin, integrin αvβ3 and tenascin-C proteins", Biomaterials, 32(4), pp. 1130-1138. (2011).

McNitt, et al., "Surface-exposed loops and an acidic patch in the Scl1 protein of group A Streptococcus enable Scl1 binding to wound-associated fibronectin", Journal of Biological Chemistry, 293(20), pp. 7796-7810. (2018).

Moschetta, et al., "Paclitaxel enhances therapeutic efficacy of the F8-IL2 immunocytokine to EDA-fibronectin-positive metastatic human melanoma xenografts", Cancer Research, 72(7), pp. 1814-1824. (2012).

Oliver-Kozup, et al., "The group A streptococcal collagen-like protein-1, Scl1, mediates biofilm formation by targeting the extra domain A-containing variant of cellular fibronectin expressed in wounded tissue", Molecular Microbiology, 87(3), pp. 672-689. (2013).

Peng, et al., "A *Streptococcus pyogenes* derived collagen-like protein as a non-cytotoxic and non-immunogenic cross-linkable biomaterial". Biomaterials 31, pp. 2755-2761. (2010).

Peng, et al., "Towards scalable production of a collagen-like protein from *Streptococcus pyogenes* for biomedical applications", Microbial Cell Factories, 11:146, 8 pages. (2012).

Reardon, et al., "A pilot study: 131I-Antitenascin monoclonal antibody 81c6 to deliver a 44-Gy resection cavity boost", Neuro-Oncology, 10(2), pp. 182-189. (2008).

Spitaleri, et al., "Phase I/II study of the tumour-targeting human monoclonal antibody-cytokine fusion protein L19-TNF in patients with advanced solid tumours", Journal of Cancer Research and Clinical Oncology, 139(3), pp. 447-455. (2013).

Villa, et al., "A high-affinity human monoclonal antibody specific to the alternatively spliced EDA domain of fibronectin efficiently targets tumor neo-vasculature in vivo", International Journal of Cancer, 122(11), pp. 2405-2413. (2008).

* cited by examiner

SEQUENCE LISTING

```
<160> NUMBER OF SEQ ID NOS: 6

<210> SEQ ID NO 1
<211> LENGTH: 361
<212> TYPE: PRT
<213> ORGANISM: Artificial Sequence
<220> FEATURE:
<223> OTHER INFORMATION: Amino acid sequence of rScl.hybrid1

<400> SEQUENCE: 1

Glu Val Ser Ser Thr Thr Met Thr Ser Ser Gln Arg Glu Ser Lys Ile
1               5                   10                  15

Lys Glu Ile Glu Glu Ser Leu Lys Lys Tyr Pro Glu Val Ser Asn Glu
            20                  25                  30

Lys Phe Trp Glu Arg Lys Trp Tyr Gly Thr Tyr Phe Lys Glu Glu Asp
        35                  40                  45

Phe Gln Lys Glu Leu Lys Asp Phe Thr Glu Lys Arg Leu Lys Glu Ile
    50                  55                  60

Leu Asp Leu Ile Gly Pro Thr Gly Leu Ala Gly Glu Lys Gly Glu Ala
65                  70                  75                  80

Gly Pro Gln Gly Glu Lys Gly Leu Pro Gly Leu Thr Gly Leu Pro Gly
                85                  90                  95
```

Leu Pro Gly Glu Arg Gly Pro Arg Gly Pro Lys Gly Asp Arg Gly Glu
                100                 105                 110

Thr Gly Ala Gln Gly Pro Ala Gly Glu Lys Gly Glu Ala Gly Pro Gln
                115                 120                 125

Gly Glu Lys Gly Leu Pro Gly Leu Thr Gly Leu Pro Gly Leu Pro Gly
            130                 135                 140

Glu Arg Gly Pro Arg Gly Pro Lys Gly Asp Arg Gly Glu Thr Gly Ala
145                 150                 155                 160

Gln Gly Pro Ala Gly Lys Ala Gly Glu Ala Gly Ala Lys Gly Glu Thr
                165                 170                 175

Gly Pro Ala Gly Pro Gln Gly Pro Arg Gly Glu Gln Gly Pro Gln Gly
                180                 185                 190

Leu Pro Gly Lys Asp Gly Glu Ala Gly Ala Gln Gly Pro Ala Gly Pro
                195                 200                 205

Met Gly Pro Ala Gly Glu Arg Gly Glu Lys Gly Glu Pro Gly Thr Gln
                210                 215                 220

Gly Ala Lys Gly Asp Arg Gly Glu Thr Gly Pro Val Gly Pro Arg Gly
225                 230                 235                 240

Glu Arg Gly Glu Ala Gly Pro Ala Gly Lys Asp Gly Glu Arg Gly Pro
                245                 250                 255

Val Gly Pro Ala Gly Lys Asp Gly Gln Asn Gly Gln Asp Gly Leu Pro
                260                 265                 270

Gly Lys Asp Gly Lys Asp Gly Gln Asn Gly Lys Asp Gly Leu Pro Gly
                275                 280                 285

Lys Asp Gly Lys Asp Gly Gln Asn Gly Lys Asp Gly Leu Pro Gly Lys
                290                 295                 300

Asp Gly Lys Asp Gly Gln Asp Gly Lys Asp Gly Leu Pro Gly Lys Asp
305                 310                 315                 320

Gly Lys Asp Gly Leu Pro Gly Lys Asp Gly Lys Asp Gly Gln Pro Gly
                325                 330                 335

Lys Pro Ala Pro Lys Thr Pro Glu Val Pro Gln Lys Pro Asp Thr Ala
                340                 345                 350

Pro Trp Ser His Pro Gln Phe Glu Lys
                355                 360

<210> SEQ ID NO 2
<211> LENGTH: 359
<212> TYPE: PRT
<213> ORGANISM: Artificial Sequence
<220> FEATURE:
<223> OTHER INFORMATION: Amino acid sequence of rScl.hybrid2

<400> SEQUENCE: 2

Asp Glu Gln Glu Glu Lys Ala Lys Val Arg Thr Glu Leu Ile Gln Glu
1                5                  10                  15

Leu Ala Gln Lys Tyr Pro Glu Val Ser Asn Glu Lys Phe Trp Glu Arg
                20                  25                  30

Lys Trp Tyr Gly Thr Tyr Phe Lys Glu Leu Thr Tyr Leu Gln Glu Arg
            35                  40                  45

Glu Gln Ala Glu Asn Ser Trp Arg Lys Arg Leu Leu Lys Gly Ile Gln
    50                  55                  60

Asp His Ala Leu Asp Gly Leu Ala Gly Glu Lys Gly Glu Ala Gly Pro
65                  70                  75                  80

Gln Gly Glu Lys Gly Leu Pro Gly Leu Thr Gly Leu Pro Gly Leu Pro
                85                  90                  95

Gly Glu Arg Gly Pro Arg Gly Pro Lys Gly Asp Arg Gly Glu Thr Gly
            100                 105                 110

Ala Gln Gly Pro Ala Gly Glu Lys Gly Glu Ala Gly Pro Gln Gly Glu
            115                 120                 125

Lys Gly Leu Pro Gly Leu Thr Gly Leu Pro Gly Leu Pro Gly Glu Arg
            130                 135                 140

Gly Pro Arg Gly Pro Lys Gly Asp Arg Gly Glu Thr Gly Ala Gln Gly
145                 150                 155                 160

Pro Ala Gly Lys Ala Gly Glu Ala Gly Ala Lys Gly Glu Thr Gly Pro
                165                 170                 175

Ala Gly Pro Gln Gly Pro Arg Gly Glu Gln Gly Pro Gln Gly Leu Pro
            180                 185                 190

Gly Lys Asp Gly Glu Ala Gly Ala Gln Gly Pro Ala Gly Pro Met Gly
            195                 200                 205

Pro Ala Gly Glu Arg Gly Glu Lys Gly Glu Pro Gly Thr Gln Gly Ala
            210                 215                 220

Lys Gly Asp Arg Gly Glu Thr Gly Pro Val Gly Pro Arg Gly Glu Arg
225                 230                 235                 240

Gly Glu Ala Gly Pro Ala Gly Lys Asp Gly Glu Arg Gly Pro Val Gly
            245                 250                 255

Pro Ala Gly Lys Asp Gly Gln Asn Gly Gln Asp Gly Leu Pro Gly Lys
            260                 265                 270

Asp Gly Lys Asp Gly Gln Asn Gly Lys Asp Gly Leu Pro Gly Lys Asp
            275                 280                 285

Gly Lys Asp Gly Gln Asn Gly Lys Asp Gly Leu Pro Gly Lys Asp Gly
            290                 295                 300

Lys Asp Gly Gln Asp Gly Lys Asp Gly Leu Pro Gly Lys Asp Gly Lys
305                 310                 315                 320

Asp Gly Leu Pro Gly Lys Asp Gly Lys Asp Gly Gln Pro Gly Lys Pro
            325                 330                 335

Ala Pro Lys Thr Pro Glu Val Pro Gln Lys Pro Asp Thr Ala Pro Trp
            340                 345                 350

Ser His Pro Gln Phe Glu Lys
            355

<210> SEQ ID NO 3
<211> LENGTH: 257
<212> TYPE: PRT
<213> ORGANISM: Artificial Sequence
<220> FEATURE:
<223> OTHER INFORMATION: Amino acid sequence of rScl1.1

<400> SEQUENCE: 3

Glu Val Ser Ser Thr Thr Met Thr Ser Ser Gln Arg Glu Ser Lys Ile
1               5                   10                  15

Lys Glu Ile Glu Glu Ser Leu Lys Lys Tyr Pro Glu Val Ser Asn Glu
            20                  25                  30

Lys Phe Trp Glu Arg Lys Trp Tyr Gly Thr Tyr Phe Lys Glu Glu Asp
        35                  40                  45

Phe Gln Lys Glu Leu Lys Asp Phe Thr Glu Lys Arg Leu Lys Glu Ile
    50                  55                  60

Leu Asp Leu Ile Gly Lys Ser Gly Ile Lys Gly Asp Arg Gly Glu Thr
65                  70                  75                  80

Gly Pro Ala Gly Pro Ala Gly Pro Gln Gly Lys Thr Gly Glu Arg Gly
            85                  90                  95

Ala Gln Gly Pro Lys Gly Asp Arg Gly Glu Gln Gly Ile Gln Gly Lys
                100                 105                 110

Ala Gly Glu Lys Gly Glu Arg Gly Glu Lys Gly Asp Lys Gly Glu Thr
            115                 120                 125

Gly Glu Arg Gly Glu Lys Gly Glu Ala Gly Ile Gln Gly Pro Gln Gly
    130                 135                 140

Glu Ala Gly Lys Asp Gly Ala Pro Gly Lys Asp Gly Ala Pro Gly Glu
145                 150                 155                 160

Lys Gly Glu Lys Gly Asp Arg Gly Glu Thr Gly Ala Gln Gly Pro Val
                165                 170                 175

Gly Pro Gln Gly Glu Lys Gly Glu Thr Gly Ala Gln Gly Pro Ala Gly
            180                 185                 190

Pro Gln Gly Glu Ala Gly Lys Pro Gly Glu Gln Gly Pro Ala Gly Pro
    195                 200                 205

Gln Gly Glu Ala Gly Gln Pro Gly Glu Lys Ala Pro Glu Lys Ser Pro
    210                 215                 220

Glu Gly Glu Ala Gly Gln Pro Gly Glu Lys Ala Pro Glu Lys Ser Lys
225                 230                 235                 240

Glu Val Thr Pro Ala Ala Glu Lys Pro Trp Ser His Pro Gln Phe Glu
                245                 250                 255

Lys

<210> SEQ ID NO 4
<211> LENGTH: 333
<212> TYPE: PRT
<213> ORGANISM: Artificial Sequence
<220> FEATURE:
<223> OTHER INFORMATION: Amino acid sequence of rScl2.28

<400> SEQUENCE: 4

Asp Glu Gln Glu Glu Lys Ala Lys Val Arg Thr Glu Leu Ile Gln Glu
1               5                   10                  15

Leu Ala Gln Gly Leu Gly Gly Ile Glu Lys Lys Asn Phe Pro Thr Leu
                20                  25                  30

Gly Asp Glu Asp Leu Asp His Thr Tyr Met Thr Lys Leu Leu Thr Tyr
            35                  40                  45

Leu Gln Glu Arg Glu Gln Ala Glu Asn Ser Trp Arg Lys Arg Leu Leu
    50                  55                  60

Lys Gly Ile Gln Asp His Ala Leu Asp Gly Gln Asp Gly Arg Asn Gly
65                  70                  75                  80

Glu Arg Gly Glu Gln Gly Pro Thr Gly Pro Thr Gly Pro Ala Gly Pro
                85                  90                  95

Arg Gly Leu Gln Gly Leu Gln Gly Leu Gln Gly Glu Arg Gly Glu Gln
            100                 105                 110

Gly Pro Thr Gly Pro Ala Gly Pro Arg Gly Leu Gln Gly Glu Arg Gly
    115                 120                 125

Glu Gln Gly Pro Thr Gly Leu Ala Gly Lys Ala Gly Glu Ala Gly Ala
    130                 135                 140

Lys Gly Glu Thr Gly Pro Ala Gly Pro Gln Gly Pro Arg Gly Glu Gln
145                 150                 155                 160

Gly Pro Gln Gly Leu Pro Gly Lys Asp Gly Glu Ala Gly Ala Gln Gly
                165                 170                 175

Pro Ala Gly Pro Met Gly Pro Ala Gly Glu Arg Gly Glu Lys Gly Glu
            180                 185                 190

```
Pro Gly Thr Gln Gly Ala Lys Gly Asp Arg Gly Glu Thr Gly Pro Val
            195                 200                 205

Gly Pro Arg Gly Glu Arg Gly Glu Ala Gly Pro Ala Gly Lys Asp Gly
210                 215                 220

Glu Arg Gly Pro Val Gly Pro Ala Gly Lys Asp Gly Gln Asn Gly Gln
225                 230                 235                 240

Asp Gly Leu Pro Gly Lys Asp Gly Lys Asp Gly Gln Asn Gly Lys Asp
            245                 250                 255

Gly Leu Pro Gly Lys Asp Gly Lys Asp Gly Gln Asn Gly Lys Asp Gly
            260                 265                 270

Leu Pro Gly Lys Asp Gly Lys Asp Gly Gln Asp Gly Lys Asp Gly Leu
            275                 280                 285

Pro Gly Lys Asp Gly Lys Asp Gly Leu Pro Gly Lys Asp Gly Lys Asp
            290                 295                 300

Gly Gln Pro Gly Lys Pro Ala Pro Lys Thr Pro Glu Val Pro Gln Lys
305                 310                 315                 320

Pro Asp Thr Ala Pro Trp Ser His Pro Gln Phe Glu Lys
            325                 330

<210> SEQ ID NO 5
<211> LENGTH: 314
<212> TYPE: PRT
<213> ORGANISM: Artificial Sequence
<220> FEATURE:
<223> OTHER INFORMATION: Amino acid sequence of rScl1.41

<400> SEQUENCE: 5

Glu Asp Ser Glu Thr Ala Thr Ala Arg Thr Lys Leu Leu Glu Lys Leu
1               5                   10                  15

Thr Glu Leu Arg Ser Gln Ser Gln Asp Arg Val Pro Gln Thr Ser Asp
            20                  25                  30

Ile Thr Gln Ala Tyr Thr Leu Trp Gly Thr Ser Tyr Asp Ser Val Glu
        35                  40                  45

Leu Tyr Lys Tyr Leu Gln Gln Ile Glu Glu Tyr Leu Gln Lys Gln Lys
50                  55                  60

Tyr His Glu Glu Gln Trp Lys Lys Glu Ile Thr Asp Gly Leu Lys Ser
65                  70                  75                  80

Gly Ala Leu Arg Gly Glu Lys Gly Glu Ala Gly Pro Gln Gly Glu Lys
            85                  90                  95

Gly Leu Pro Gly Leu Thr Gly Leu Pro Gly Leu Pro Gly Glu Arg Gly
            100                 105                 110

Pro Arg Gly Pro Lys Gly Asp Arg Gly Glu Thr Gly Ala Gln Gly Pro
            115                 120                 125

Val Gly Pro Gln Gly Glu Lys Gly Glu Ala Gly Thr Pro Gly Lys Asp
        130                 135                 140

Gly Leu Arg Gly Pro Gln Gly Asp Pro Gly Ala Pro Gly Lys Asp Gly
145                 150                 155                 160

Ala Pro Gly Glu Lys Gly Asp Arg Gly Glu Thr Gly Ala Gln Gly Pro
            165                 170                 175

Val Gly Pro Gln Gly Glu Lys Gly Glu Ala Gly Thr Pro Gly Lys Asp
            180                 185                 190

Gly Ala Pro Gly Glu Lys Gly Glu Lys Gly Asp Arg Gly Glu Thr Gly
            195                 200                 205

Ala Thr Gly Ala Gln Gly Pro Gln Gly Glu Ala Gly Lys Asp Gly Ala
        210                 215                 220
```

```
Gln Gly Pro Val Gly Pro Gln Gly Glu Lys Gly Glu Thr Gly Ala Gln
225                 230                 235                 240

Gly Pro Ala Gly Pro Gln Gly Glu Lys Gly Glu Thr Gly Ala Gln Gly
                245                 250                 255

Pro Ala Gly Pro Gln Gly Glu Ala Gly Gln Pro Gly Glu Lys Ala Pro
            260                 265                 270

Glu Lys Ser Pro Glu Val Thr Pro Thr Pro Glu Met Pro Glu Gln Pro
        275                 280                 285

Gly Glu Gln Ala Pro Glu Lys Ser Lys Glu Val Thr Pro Ala Pro Glu
        290                 295                 300

Lys Pro Trp Ser His Pro Gln Phe Glu Lys
305                 310

<210> SEQ ID NO 6
<211> LENGTH: 6
<212> TYPE: PRT
<213> ORGANISM: Artificial Sequence
<220> FEATURE:
<223> OTHER INFORMATION: Integrin recognition sequence

<400> SEQUENCE: 6

Gly Leu Pro Gly Glu Arg
1               5
```

TARGETING TUMOR MICROENVIRONMENTS WITH RECOMBINANT PROKARYOTIC COLLAGEN-LIKE PROTEINS

GOVERNMENT LICENSE RIGHTS

This invention was made with government support under NSF Award Number: DGE1144676 awarded by the National Science Foundation. The government has certain rights in the invention.

TECHNICAL FIELD

Various embodiments disclosed herein relate generally to various recombinant prokaryotic collagen-like or triple helical proteins, methods of manufacture and use.

BACKGROUND

The concept of drug delivery to tumors holds promise for improved therapeutics, enabling specific delivery of drugs and biologics to pathological tissue, thereby avoiding off-target effects, and reducing the toxicity of currently used therapies. To target these sites, drugs are conjugated to carriers that recognize the tumor microenvironment, such as overexpressed cell-surface and secreted markers.

However, current cancer biomarkers still pose a significant off-target risk due to their expression on healthy cells.

Collagens are major structural proteins present in the extracellular matrix (ECM) of animals. They are defined by a characteristic triple-helix structure that requires a (Gly-Xaa-Yaa), repeating sequence. The residues found in the Xaa and Yaa positions are commonly proline, where Pro in the Yaa position in mammalian collagens is post-translationally modified to hydroxyproline (Hyp) which enhances helical stability. Prokaryotic collagen-like proteins form stable triple helices without the presence of hydroxyprolines and have been shown to be expressed in several bacteria, including *Streptococcus pyogenes* and filaments on *Bacillus anthracis* spores.

Fibronectin is a high molecular weight glycoprotein of the ECM and is found throughout the human body in two main forms. Plasma fibronectin, which is produced by hepatocytes in the liver, is secreted in a soluble form into the blood stream, whereas cellular fibronectin (cFn), is produced by a variety of cells, including fibroblasts, and is deposited as an insoluble crosslinked protein in tissues. Humans express over 20 cFn isoforms due to alternative splicing of a single fibronectin gene, FN1, that differ from plasma fibronectin by the inclusion of additional fibronectin type III repeats, extra domains A (EDA/EIIIA), B (EDB/EIIIB) and the variable connecting segments (VCS). Specifically, EDA/cFn and EDB/cFn are expressed during embryogenesis but only at negligent levels in normal adult tissue. However, the expression of both EDA/cFn and EDB/cFn isoforms is substantially upregulated within the tumor microenvironment. Similarly, Tenascin-C (TNC) is a related ECM protein that contains fibronectin type III repeats and has a similar expression pattern to EDA/cFn and EDB/cFn. Thus, EDA- and EDB-containing cFn isoforms, as well as TNC, are attractive biomarkers for targeting the tumor microenvironment.

Antibodies that are able to target EDA and EDB cFn isoforms have been designed, wherein such antibodies are conjugated with pro-inflammatory cytokines to illicit an immune response against cancerous cells. Antibodies, aptamers and small immunoreactive proteins (SIPs) have also been designed to target TNC in tumors. However, antibodies are mono-specific and cannot target more than one tumor-associated ligand at the same time. Additionally, antibody production is costly and time-consuming.

The streptococcal collagen-like protein-1 (Scl1) is a ubiquitous surface adhesin, which is co-expressed with a range of known virulence factors that are regulated by the multiple virulence gene regulator of Group A Streptococcus (GAS). Scl1 is a homotrimeric protein protruding from the GAS surface that contains four structurally distinct regions. The outermost N-terminal variable (V) region is adjacent to a collagen-like (CL) region that consists of a varying number of GlyXaaYaa (GXY) repeats and adopts stable collagen-like triple helices. At the C-terminus, Scl1 contains a linker (L) region which is a series of conserved, direct repeats adjoining the CL region to the cell wall/membrane (WM)-associated region. Functionally, Scl1 has been shown to bind host-cell integrin receptors and plasma components. Scl1 has also been shown to bind to cellular fibronectin, but not plasma fibronectin. Scl1 is also recognized to play a significant role in biofilm formation on abiotic surfaces.

The inventors have discovered that recombinant proteins derived from bacterial collagen-like proteins, such as Scl1, can serve as effective tools for targeting the tumor microenvironment.

SUMMARY OF EXEMPLARY EMBODIMENTS

Various embodiments recite a recombinant collagen-like protein, wherein the protein includes a binding domain having the capacity to bind to both extra domain A and extra domain B-containing variants of cellular fibronectin. In various embodiments, the collagen-like protein is a prokaryotic collagen-like protein, such as a streptococcal collagen-like protein from a Group A *Streptococcus*. In various embodiments, the Group A *Streptococcus* is *Streptococcus pyogenes*. In various embodiments, the streptococcal collagen-like protein is a variant of Scl1 or Scl2 of *S. pyogenes* or a combination thereof.

Various embodiments also recite a recombinant collagen-like protein further having a capacity to bind to Tenascin-C.

Various embodiments also recite a recombinant collagen-like protein, wherein the collagen-like protein further recognizes collagen-binding integrin receptors $\alpha_2\beta_1$ and $\alpha_{11}\beta_1$.

Various embodiments recite a recombinant collagen-like protein having an amino acid sequence of SEQ ID NO: 1 or SEQ ID NO: 2.

Various embodiments also recite an expression vector including a nucleotide sequence encoding the recombinant collagen-like protein.

Various embodiments also recite a host cell including an expression vector including a nucleotide sequence encoding the recombinant collagen-like protein.

Various embodiments recite pharmaceutical compositions including a recombinant collagen-like protein, wherein the protein includes a binding domain having the capacity to bind to both extra domain A and extra domain B-containing variants of cellular fibronectin.

Various embodiments also recite a method of treating cancer that involves administering a recombinant collagen-like protein, wherein the protein includes a binding domain having a capacity to bind to both extra domain A and extra domain B-containing variants of cellular fibronectin.

Various embodiments also recite a method of treating cancer that involves administering a recombinant collage-like protein having an amino acid sequence of SEQ ID NO: 1 or SEQ ID NO: 2.

Various embodiments also recite a method of preparing a collagen-like protein including a binding domain having the capacity to bind to both extra domain A and extra domain B-containing variants of cellular fibronectin that involves combining (i) two copies of an integrin recognition sequence GLPGER inserted into the collagen-like (CL) domain of a protein of SEQ ID NO: 4; and (ii) the variable (V) domain from a protein of SEQ ID NO: 3.

BRIEF DESCRIPTION OF THE DRAWINGS

In order to better understand various embodiments, reference is made to the accompanying drawings, wherein.

To facilitate understanding, identical reference numerals have been used to designate elements having substantially the same or similar structure or substantially the same or similar function.

DETAILED DESCRIPTION

The description and drawings presented herein illustrate various principles. It will be appreciated that those skilled in the art will be able to devise various arrangements that, although not explicitly described or shown herein, embody these principles and are included within the scope of this disclosure. As used herein, the term, "or" refers to a non-exclusive or (i.e., and/or), unless otherwise indicated (e.g., "or else" or "or in the alternative"). Additionally, the various embodiments described herein are not necessarily mutually exclusive and may be combined to produce additional embodiments that incorporate the principles described herein.

This disclosure relates to defined isoforms of the extracellular matrix (ECM) protein, cellular fibronectin (cFn) and Tenascin-C (TNC) as biomarkers for the delivery of drugs to the tumor microenvironment. This disclosure further relates to recombinant proteins derived from bacterial collagen-like proteins that may serve as effective tools for targeting the tumor microenvironment In some embodiments, the bacterial collagen-like protein is derived from a prokaryotic collagen-like protein, such as a Streptococcal collagen-like protein. In some embodiments, the Streptococcal collagen-like protein is selected from a group that includes an Scl1 or Scl2 protein, a variant of an Scl1 or Scl2 protein, or combinations thereof.

In various embodiments, the collagen-like proteins may be designed to have binding capacity for isoforms of the extracellular matrix (ECM) protein, cellular fibronectin (cFn) and Tenascin-C (TNC) that may be found within the tumor microenvironment. In various embodiments, the collagen-like proteins may be designed to have binding capacity for extra-domain A isoforms of cellular fibronectin (EDA/cFn), extra-domain B isoforms of cellular fibronectin (EDB/cFn), TNC isoforms, or combinations thereof.

In various embodiments, the collagen-like proteins may further have binding capacity for integrin receptors. In some embodiments, the collagen-like proteins may be designed to have binding capacity to $\alpha_2\beta_1$ and $\alpha_{11}\beta_1$ receptors that are upregulated on cancer cells.

In various embodiments, the collagen-like protein may include an rScl1 construct composed of a rod-shaped collagen-like domain (CL) and a globular variable (V) domain, as shown in FIG. 1. In various embodiments, the rScl1 construct may be designed to bind to at least one isoform of cellular fibronectin, selected from the group consisting of EDA/cFn, EDB/cFn and TNC, and promote human cell attachment through collagen receptors, integrins $\alpha_2\beta_1$ and $\alpha_{11}\beta_1$.

In various embodiments, the collagen-like protein may include a recombinant Scl1 hybrid construct characterized by SEQ ID NO: 1. In another embodiment, the collagen-like protein may include a recombinant Scl1 hybrid construct characterized by SEQ ID NO: 2.

In some embodiments, the recombinant Scl1 constructs may be derived from a parental Scl1 sequence. In certain embodiments, the recombinant Scl1 constructs are derived from parental Scl1 sequences of SEQ ID NOS: 3-5. In one embodiment, the parental Scl sequence rScl1.1 of SEQ ID NO: 3 is derived from the scl1 allele from a wild-type M1 serotype strain of group A *Streptococcus* (GAS). The amino acid sequence of rScl1.1 is the same as the sequence in the genome of M1, however, the rScl1 proteins lack the C-terminally located Linker and Cell Wall Attachment Domains found in the endogenous protein. In another embodiment, the parental Scl sequence rScl2.28 of SEQ ID NO: 4 is derived from the scl2 allele from a wild-type M28 serotype strain of GAS. The amino acid sequence of rScl2.28 is the same as the sequence in the genome of M28, however, the rScl2 proteins lack the C-terminal Cell Wall Attachment Domain found in the endogenous protein. In another embodiment, the parental Scl sequence rScl1.41 of SEQ ID NO: 5 is derived from the scl1 allele from a wild-type M41 serotype strain of GAS. The amino acid sequence of rScl1.41 is the same as the sequence in the genome of M41, however, the rScl1 proteins lack the C-terminally located Linker and Cell Wall Attachment Domains found in the endogenous protein.

In an exemplary embodiment, the rScl.hybrid1 construct (SEQ ID NO: 1) shown in FIG. 1 may be designed to have two desired biological functions: (i) 2 copies of the integrin recognition sequence ((GLPGER (SEQ ID NO: 6)) placed into the inert CL domain of rScl2.28 (SEQ ID NO: 4); and (ii) the V domain from the TNC and EDA/EDB-binding protein rScl1.1 (SEQ ID NO: 3). The $(GLPGER)_2$-CL domain was found to promote efficient internalization of group A *Streptococcus* expressing the rScl1.1 protein, compared to group A Streptococcus that expresses inert rScl2.28. In this embodiment, the V domain of rScl1.1, specifically the loop-region of Scl1.1-V domain, binds to EDA/cFn and to rEDB and TNC. Thus, in this embodiment, the rScl.hybrid1 construct possess both the capacity to bind to TNC, as well as EDA/cFn and EDB/cFn isoforms, highly expressed within and around tumor/cancerous tissues, as well as the capacity to promote internalization via integrin receptors $\alpha_2\beta_1$ and $\alpha_{11}\beta_1$.

The hybrid Scl1 proteins substantially described in FIG. 1 differ from current TNC and EDA/EDB targeting technologies due to their capacity to target a combination of biomarkers that include TNC, and both of EDA/cFn and EDB/cFn, as well as recognize collagen-binding integrin receptors $\alpha_2\beta_1$ and $\alpha_{11}\beta_1$, enabling both tissue localization and internalization of conjugated drugs, cytokines, and siRNAs. In contrast, antibody therapies are only able to target 1 ligand per antibody.

In various embodiments, the hybrid Scl1 proteins of the invention may be produced using any suitable expression system, including 6x His-tag expression systems and strep-tag expression systems. In various embodiments, the expression vector comprises a nucleotide sequence encoding the hybrid Scl1 proteins of the invention.

In various embodiments, there is provided a host cell comprising and expressing an expression vector having a nucleotide sequence encoding the hybrid Scl1 proteins of the invention. Suitable host cells include prokaryotic cells, such as *Escherichia coli, Streptococcus* and *Bacillus*.

In various embodiments, the collagen-like proteins may be conjugated to a therapeutic agent. In some embodiments, the collagen-like protein may form conjugates with various therapeutic agents used in the treatment of cancer, such as chemotherapeutic agents. Exemplary chemotherapeutic agents include busulfan, improsulfan, piposulfan, benzodepa, carboquone, meturedepa, uredepa, altretamine, triethylenemelamine, triethylenephosphoramide, triethylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluorouracil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, elfornithine, elliptinium acetate, etoglucid, etoposide, flutamide, gallium nitrate, hydroxyurea, interferon-alpha, interferon-beta, interferon-gamma, interleukin-2, lentinan, lonidamine, mitoguazone, mitoxantrone, mopidamol, nitracrine, pentostatin, phenamet, pirarubicin, podophyllinic acid, 2-ethylhydrazide, procarbazine, razoxane, sizofiran, spirogermanium, paclitaxel, tamoxifen, teniposide, tenuazonic acid, triaziquone, 2,2',2"-trichlorotriethylamine, urethan, vinblastine, vincristine, and vindesine.

The present disclosure further relates to pharmaceutical compositions containing the recombinant collagen-like proteins of the invention. In some embodiments, the recombinant collagen-like protein may be formulated in admixture with a pharmaceutically acceptable carrier. The carrier may take a wide variety of forms depending on the form of preparation desired for administration, e.g., oral or parenteral (including intravenous). In a preferred embodiment, the carrier is a nanoparticle. In a more preferred embodiment, the pharmaceutical composition contains a nanoparticle coated with the recombinant collagen-like protein of the invention.

Another aspect of the present disclosure provides a method of treating cancer that involves administering a therapeutically effective amount of the collagen-like proteins of the invention. In various embodiments, the collagen-like proteins of the invention may be used to treat growing tumors as well as metastatic cancers. Exemplary types of cancer include breast cancer, prostate cancer, melanoma, gastric cancers, colorectal cancer, and head and neck cancers.

EXAMPLE 1

Production Method of rScl1 Hybrid Proteins rScl proteins are produced in *E. coli*, and expressed either intracellularly or in the periplasmic space. The extracellular fraction is recovered from culture supernatant following precipitation with ammonium sulphate. Production yields vary between rScl1 constructs, ranging from 1-20 milligrams of protein per liter of culture.

Sequences encoding the rScl.hybrid1 and rScl.hybrid2 proteins were cloned and expressed in an *E. coli* Strep-tag II system. The hybrid proteins were recovered from *E. coli* following incubation in a high-sucrose buffer or via cell lysis, and then purified by affinity chromatography, using StrepTactin Sepharose. The proteins were then subjected to dialysis to desired exchange buffers and stored at −20° C.

EXAMPLE 2

Construction of Recombinant rScl Hybrid Proteins 1 and 2

Recombinant rScl.hybrid1 and rScl.hybrid2 constructs were generated by several sequential manipulations. Both proteins were derived from rScl proteins rScl1.1, rScl1.41 and rScl2.28. Construct rScl.hybrid1 harbors a CL-domain that contains tandem integrin-binding motifs ((GLPGER)$_2$) recloned from the CL-domain of rScl1.41 into the biologically inert CL-domain of rScl2.28, and the V-domain of rScl1.1 with ECM (EDA/cFn, EDB/cFn, and TNC) binding domain.

The rScl.hybrid2 protein is comprised of the CL-domain of rScl.hybrid1 and the rScl2.28 V-domain modified to contain the ECM-binding domain.

EXAMPLE 3

Binding of rScl Proteins to rEDA, rEDB and TNC

Figure 1:
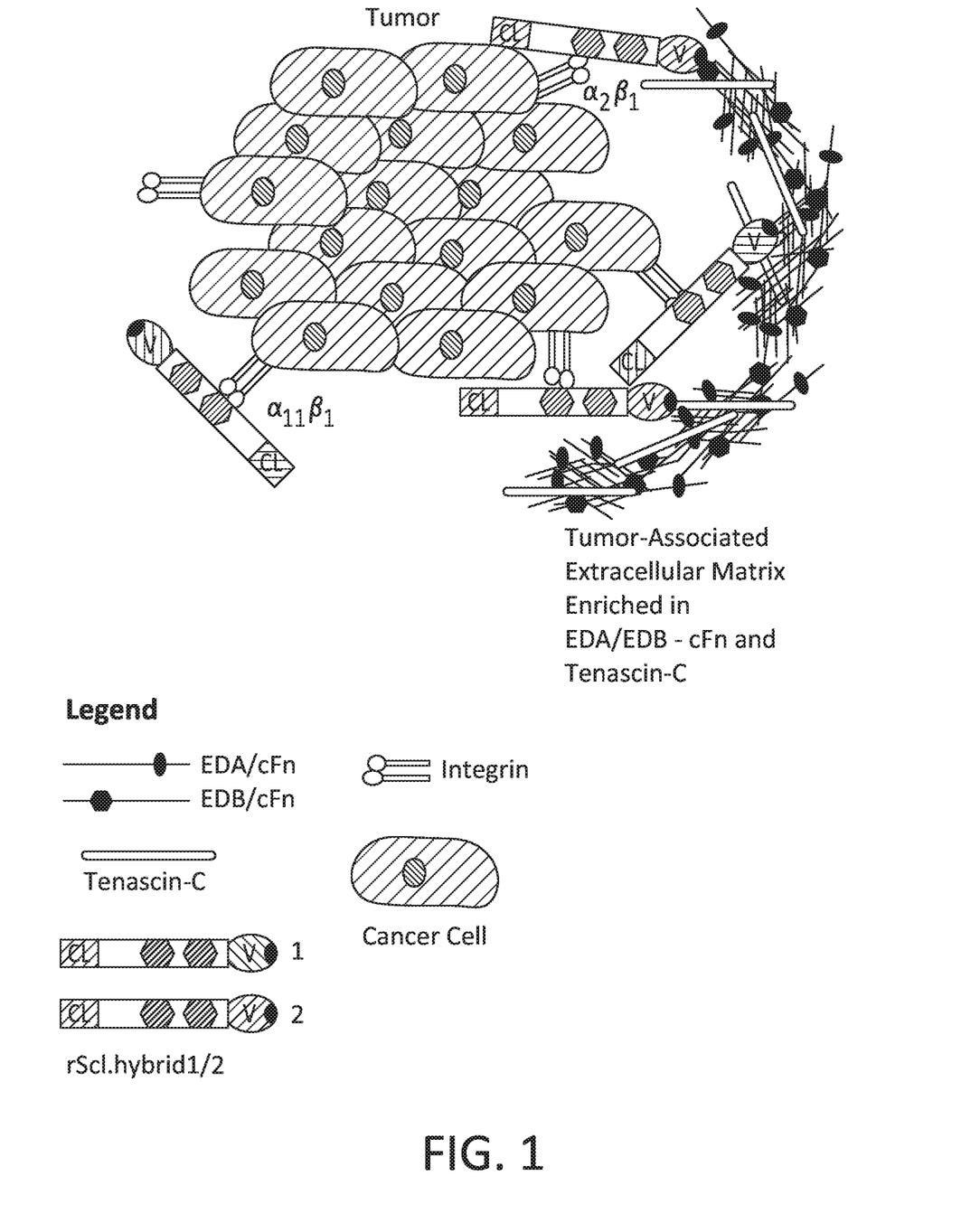
FIG. 1 illustrates a model of rScl hybrid constructs as targeting agents to the tumor microenvironment.
Figure 2A:
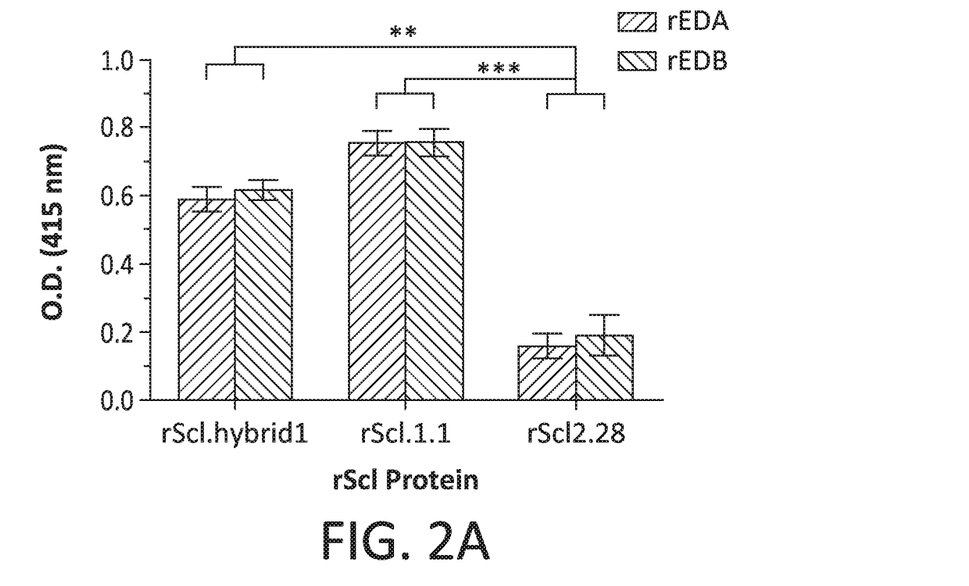
FIGS. 2A and 2B illustrate the binding of rScl hybrid constructs to recombinant rEDA, rEDB and Tenascin-C.
Figure 2B:
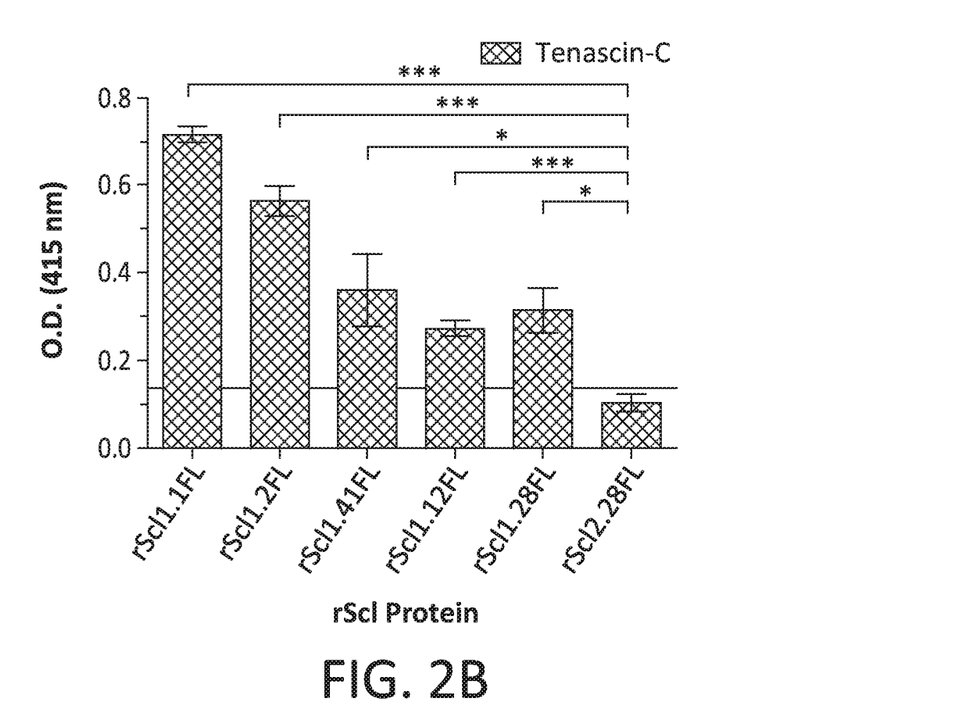
Figure 3:
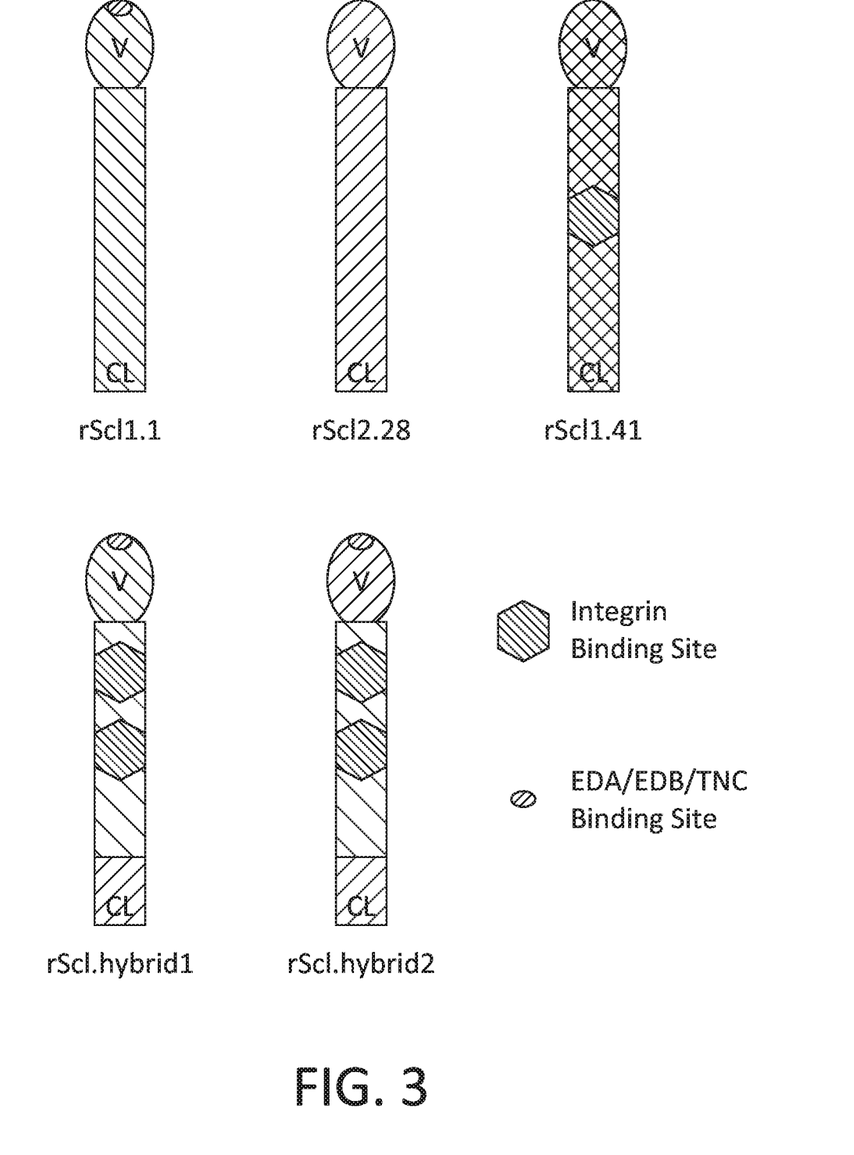
FIG. 3 illustrates the structure of rScl hybrid constructs 1 and 2.

Recombinant Scl1 proteins were tested for binding to recombinant EDA and EDB (FIG. 2A), as well as Tenascin-C (FIG. 2B). rScl proteins were immobilized onto StrepTactin-coated microplate wells and incubated with rEDA/rEDB or TNC. Primary anti-rEDB or TNC antibodies and HRP-conjugated secondary antibodies were used for ligand detection. The shown graphic bars indicate mean $OD_{415nm}$ normalized against BSA controls. FIG. 2A shows that both rScl1.1 protein derived from a natural sequence and the engineered rScl.hybrid1 recognize recombinant EDB to a comparable level as recombinant EDA. FIG. 2B shows ELISA binding data between rScl1 proteins and TNC extracted from glioblastoma cancer cells.

Although the various embodiments have been described in detail with particular reference to certain aspects thereof, it should be understood that the invention is capable of other embodiments and its details are capable of modifications in various obvious respects. As is readily apparent to those skilled in the art, variations and modifications can be effected while remaining within the spirit and scope of the invention. Accordingly, the foregoing disclosure, description, and figures are for illustrative purposes only and do not in any way limit the invention, which is defined only by the claims.

```
Amino acid sequence of rScl.hybrid1
                                             SEQ ID NO: 1
EVSSTTMTSSQRESKIKEIEESLKKYPEVSNEKFWERKWYGTYFKEEDFQ

KELKDFTEKRLKEILDLIGPTGLAGEKGEAGPQGEKGLPGLTGLPGLPGE

RGPRGPKGDRGETGAQGPAGEKGEAGPQGEKGLPGLTGLPGLPGERGPRG

PKGDRGETGAQGPAGKAGEAGAKGETGPAGPQGPRGEQGPQGLPGKDGEA

GAQGPAGPMGPAGERGEKGEPGTQGAKGDRGETGPVGPRGERGEAGPAGK

DGERGPVGPAGKDGQNGQDGLPGKDGKDGQNGKDGLPGKDGKDGQNGKDG

LPGKDGKDGQDGKDGLPGKDGKDGLPGKDGKDGQPGKPAPKTPEVPQKPD

TAPWSHPQFEK

Amino acid sequence of rScl.hybrid2
                                             SEQ ID NO: 2
DEQEEKAKVRTELIQELAQKYPEVSNEKFWERKWYGTYFKFLTYLQEREQ

AENSWRKRLLKGIQDHALDGLAGEKGEAGPQGEKGLPGLTGLPGLPGERG

PRGPKGDRGETGAQGPAGEKGEAGPQGEKGLPGLTGLPGLPGERGPRGPK

GDRGETGAQGPAGKAGEAGAKGETGPAGPQGPRGEQGPQGLPGKDGEAGA

QGPAGPMGPAGERGEKGEPGTQGAKGDRGETGPVGPRGERGEAGPAGKDG

ERGPVGPAGKDGQNGQDGLPGKDGKDGQNGKDGLPGKDGKDGQNGKDGLP

GKDGKDGQDGKDGLPGKDGKDGLPGKDGKDGQPGKPAPKTPEVPQKPDTA

PWSHPQFEK

Amino acid sequence of rScl1.1
                                             SEQ ID NO: 3
EVSSTTMTSSQRESKIKFIEESLKKYPEVSNEKFWERKWYGTYFKEEDFQ

KFLKDFTEKRLKEILDLIGKSGIKGDRGETGPAGPAGPQGKTGERGAQGP

KGDRGEQGIQGKAGEKGERGEKGDKGETGERGEKGEAGIQGPQGEAGKDG

APGKDGAPGEKGEKGDRGETGAQGPVGPQGEKGETGAQGPAGPQGEAGKP

GEQGPAGPQGEAGQPGEKAPEKSPEGEAGQPGEKAPEKSKEVTPAAEKPW

SHPQFEK

Amino acid sequence of rScl2.28
                                             SEQ ID NO: 4
DEQEEKAKVRTELIQELAQGLGGIEKKNFPTLGDEDLDHTYMTKLLTYLQ

EREQAENSWRKRLLKGIQDHALDGQDGRNGERGEQGPTGPTGPAGPRGLQ

GLQGLQGERGEQGPTGPAGPRGLQGERGEQGPTGLAGKAGEAGAKGETGP

AGPQGPRGEQGPQGLPGKDGEAGAQGPAGPMGPAGERGEKGEPGTQGAKG

DRGETGPVGPRGERGEAGPAGKDGERGPVGPAGKDGQNGQDGLPGKDGKD

GQNGKDGLPGKDGKDGQNGKDGLPGKDGKDGQDGKDGLPGKDGKDGLPGK

DGKDGQPGKPAPKTPEVPQKPDTAPWSHPQFEK

Amino acid sequence of rScl1.41
                                             SEQ ID NO: 5
EDSETATARTKLLEKLTELRSQSQDRVPQTSDITQAYTLWGTSYDSVELY

KYLQQIEEYLQKQKYHEEQWKKEITDGLKSGALRGEKGEAGPQGEKGLPG

LTGLPGLPGERGPRGPKGDRGETGAQGPVGPQGEKGEAGTPGKDGLRGPQ

GDPGAPGKDGAPGEKGDRGETGAQGPVGPQGEKGEAGTPGKDGAPGEKGE

KGDRGETGATGAQGPQGEAGKDGAQGPVGPQGEKGETGAQGPAGPQGEKG

ETGAQGPAGPQGEAGQPGEKAPEKSPEVTPTPEMPEQPGEQAPEKSKFVT

PAPEKPWSHPQFEK

Integrin recognition sequence
                                             SEQ ID NO: 6
GLPGER
```

The invention claimed is:

1. A recombinant collagen-like protein comprising a binding domain having binding capacity for both extra domain A and extra domain B-containing variants of cellular fibronectin,
wherein the protein comprises:
a recombinant collagen-like (CL)-domain, and
a variable (V)-domain comprising an ECM-binding domain from a streptococcal Scl1.1 protein;
wherein the recombinant CL-domain is a CL-domain from a streptococcal Scl2.28 protein;
wherein the CL-domain from the streptococcal Scl2.28 protein is modified to include an integrin recognition sequence from the CL-domain of the streptococcal Scl1.41 protein.

2. The recombinant collagen-like protein of claim 1, wherein:
the protein is a streptococcal collagen-like protein from a Group A *Streptococcus*, and
the Group A *Streptococcus* is *Streptococcus pyogenes*.

3. The recombinant collagen-like protein of claim 1, wherein the protein further comprises binding capacity for Tenascin-C.

4. The recombinant collagen-like protein of claim 1, wherein the protein recognizes collagen-binding integrin receptors $\alpha_2\beta_1$ and $\alpha_{11}\beta_1$.

5. The recombinant collagen-like protein of claim 1, wherein the protein comprises two copies of an integrin recognition sequence GLPGER.

6. The recombinant collagen-like protein of claim 5, wherein the protein comprises the variable domain of the rScl1.1 sequence of SEQ ID NO: 3.

7. A recombinant collagen-like protein comprising an amino acid sequence selected from the group consisting of SEQ ID NO: 1 and SEQ ID NO: 2.

8. A pharmaceutical composition comprising
the recombinant collagen-like protein of claim 7; and
a pharmaceutically acceptable carrier.

9. The composition of claim 8, wherein the carrier is a nanoparticle.

10. The composition of claim 9, wherein the nanoparticle is coated with the collagen-like protein.

11. A recombinant collagen-like protein comprising a binding domain having binding capacity for both extra domain A and extra domain B-containing variants of cellular fibronectin,
wherein the protein comprises:
a recombinant collagen-like (CL)-domain, and
a variable (V)-domain;
wherein:
the recombinant CL-domain is a CL-domain from a streptococcal Scl2.28 protein, and
the CL-domain from the streptococcal Scl2.28 protein is modified to include two integrin recognition sequences from the CL-domain of the streptococcal Scl1.41 protein.

12. The recombinant collagen-like protein of claim 11, wherein the two integrin recognition sequences each comprise SEQ ID NO: 6.

13. The recombinant collagen-like protein of claim 11, wherein:
the variable (V)-domain comprises an ECM-binding domain from a streptococcal Scl1.1 protein; or
the variable (V)-domain is a variable domain from a streptococcal Scl1.1 protein.

14. A method of targeting a cancer in a patient in need thereof, comprising administering a recombinant collagen-like protein of claim 7 to the patient.

15. A method of treating cancer in a patient in need thereof, comprising administering a recombinant collagen-like protein of claim 1 to the patient, wherein the collagen-like protein is conjugated with a therapeutic agent useful for the treatment of cancer.

16. A method of targeting a cancer in a patient in need thereof, comprising administering a recombinant collagen-like protein of claim 7 to the patient, wherein the cancer is selected from a group consisting of a tumor or a metastatic cancer.

17. A method of treating cancer in a patient in need thereof, comprising administering a recombinant collagen-like protein of claim 7 to the patient, wherein the cancer is selected from a group consisting of breast cancer, prostate cancer, melanoma, gastric cancer, colorectal cancer, and head and neck cancer, wherein the collagen-like protein is conjugated with a therapeutic agent useful for the treatment of cancer.

18. A method of preparing a collagen-like protein comprising a binding domain having the capacity to bind to both extra domain A and extra domain B-containing variants of cellular fibronectin comprising the steps of combining:
 (i) two copies of an integrin recognition sequence of SEQ ID NO: 6 inserted into the collagen-like (CL) domain of a protein of SEQ ID NO: 4; and
 (ii) the variable (V)-domain from a protein of SEQ ID NO: 3.

* * * * *